United States Patent
Cowan et al.

(10) Patent No.: US 6,780,822 B2
(45) Date of Patent: Aug. 24, 2004

(54) ANHYDRIDE-MODIFIED CHITOSAN, METHOD OF PREPARATION THEREOF, AND FLUIDS CONTAINING SAME

(75) Inventors: Jack C. Cowan, Lafayette, LA (US); Roy F. House, Houston, TX (US); Tammy L. Rodrigue, St. Martinville, LA (US)

(73) Assignee: Venture Chemicals, Inc., Lafayette, LA (US)

( * ) Notice: Subject to any disclaimer, the term of this patent is extended or adjusted under 35 U.S.C. 154(b) by 0 days.

(21) Appl. No.: 10/348,524

(22) Filed: Jan. 21, 2003

(65) Prior Publication Data

US 2003/0153467 A1 Aug. 14, 2003

Related U.S. Application Data

(63) Continuation-in-part of application No. 10/035,262, filed on Jan. 3, 2002, now Pat. No. 6,656,885, which is a continuation-in-part of application No. 09/782,633, filed on Feb. 13, 2001, now Pat. No. 6,358,889, which is a continuation-in-part of application No. 09/222,293, filed on Dec. 28, 1998, now Pat. No. 6,258,755.

(51) Int. Cl.$^7$ .............................. C09K 7/02; C08B 37/08
(52) U.S. Cl. .................. 507/110; 536/20; 536/55.3
(58) Field of Search ............................ 507/110; 536/20, 536/55.3

(56) References Cited

U.S. PATENT DOCUMENTS

| | | | | |
|---|---|---|---|---|
| 3,879,376 | A | * | 4/1975 | Vanlerberghe et al. ......... 536/20 |
| 3,953,608 | A | * | 4/1976 | Vanlerberghe et al. ....... 514/777 |
| 4,996,307 | A | * | 2/1991 | Itoi et al. ....................... 536/20 |
| 5,874,551 | A | * | 2/1999 | Glasser et al. ................ 536/20 |
| 6,258,755 | B1 | * | 7/2001 | House et al. ................ 507/110 |
| 6,291,404 | B2 | * | 9/2001 | House ......................... 507/110 |
| 6,358,889 | B2 | * | 3/2002 | Waggenspack et al. ..... 507/110 |
| 6,509,039 | B1 | * | 1/2003 | Nies ........................... 424/488 |

* cited by examiner

*Primary Examiner*—Philip C. Tucker
(74) *Attorney, Agent, or Firm*—Roy F. House

(57) ABSTRACT

The invention provides an organic diacid anhydride-modified chitosan and a method of preparing the same under high shear conditions which eliminates the use of solvents and excessive amounts of aqueous liquids. Also provided are organic diacid anhydride-modified chitosans containing an inorganic basic material which enhances the aging stability thereof. The invention also provides fluids useful in various well drilling and servicing operations comprising an alkaline aqueous liquid containing an organic diacid anhydride-modified chitosan, as well as a method of drilling wells therewith.

15 Claims, No Drawings

ANHYDRIDE-MODIFIED CHITOSAN, METHOD OF PREPARATION THEREOF, AND FLUIDS CONTAINING SAME

The present patent application is a continuation-in-part application of patent application Ser. No. 10/035,262 filed Jan. 3, 2002 now U.S. Pat. No. 6,656,885, incorporated herein by reference, which is a continuation-in-part application of patent application Ser. No. 09/782,633 filed Feb. 13, 2001, now U.S. Pat. No. 6,358,889, incorporated herein by reference, which is a continuation-in-part application of patent application Ser. No. 09/222,293 filed Dec. 28, 1998, now U.S. Pat. No. 6,258,755.

This invention was made with Government support under Award No. DMI-9901868 awarded by the National Science Foundation. The Government has certain rights in this invention.

FIELD OF THE INVENTION

The invention pertains to the modification of chitosan to produce viscosifiers (thickeners) for aqueous liquids, and to viscosified aqueous fluids containing such modified chitosans dispersed therein, and to methods of drilling a well utilizing such fluids.

BACKGROUND OF THE INVENTION

Many viscosifiers for, and methods of, increasing the viscosity of aqueous liquids are known. Such viscosifiers may be so-called water-soluble polymers such as biopolymers, gums, cellulose derivatives, alginates, and other polysaccharides or polysaccharide derivatives, and various synthetic polymers. Representative polymers are set forth in the book "Handbook of Water Soluble Gums and Resins," Robert L. Davidson, Ed., 1980.

Viscoelastic fluids are characterized as having a rheological profile which is shear thinning, having a high viscosity at extremely low shear rates and a low viscosity at high shear rates. Thus such fluids are pseudoplastic having a high yield stress.

This type of rheology is produced by hydrating in the fluid certain water soluble polymers or other colloidal materials. These polymers presently known are biopolymers, i.e., microbially produced polysaccharides or heteropolysaccharides, and are well known in the art.

There is a need for fluids which exhibit a high low shear rate viscosity which are shear thinning.

Chitosan is a partially or fully deacetylated form of chitin, a naturally occurring polysaccharide. Structurally, chitin is a polysaccharide consisting of beta-(1→4)2-acetamido-2-deoxy-D-glucose units, some of which are deacetylated. The degree of deacetylation usually varies between 8 and 15 percent, but depends on the species from which the chitin is obtained, and the method used for isolation and purification.

Chitin is not one polymer with a fixed stoichiometry, but a class of polymers of N-acetylglucosamine with different crystal structures and degrees of deacetylation, and with fairly large variability from species to species. The polysaccharide obtained by more extensive deacetylation of chitin is chitosan.

Like chitin, chitosan is a generic term for a group of polymers of acetylglucosamine, but with a degree of deacetylation of between 50 and 100 percent. Chitosan is the beta-(1-4)-polysaccharide of D-glucosamine, and is structurally similar to cellulose, except that the C-2 hydroxyl group in cellulose is substituted with a primary amine group in chitosan. The large number of free amine groups (pKa=6.3) makes chitosan a polymeric weak base. Both chitin and chitosan are insoluble in water, dilute aqueous bases, and most organic solvents. However, unlike chitin, chitosan is soluble in dilute aqueous acids, usually carboxylic acids, as the chitosonium salt. Solubility in dilute aqueous acid is therefore a simple way to distinguish chitin from chitosan.

Chitosan is unique in that it is a polysaccharide containing primary amine groups. Chitosan forms water-soluble salts with many organic and inorganic acids.

It is known to prepare chitosan derivatives by attaching various groups to one or more hydroxyl groups of the chitosan, as in various cellulose derivatives, and/or in attaching various groups to the primary amino group of chitosan.

U.S. Pat. Nos. 3,879,376 and 3,953,608 disclose chitosan derivatives formed by acylation of chitosan with a saturated or unsaturated organic diacid anhydride. The chitosan derivatives contain 5 to 30% acetylglucosamine, 5 to 40% glucosamine, and 30 to 90% of glucosamine units reacted with the diacid anhydride. The derivatives are prepared in an aqueous dispersion. They may be recovered by the addition of a solvent such as an alcohol to precipitate the derivative. The derivatives are useful in various cosmetic compositions.

U.S. Pat. No. 4,996,307 discloses the preparation of an acylated chitosan having a degree of acylation of 35 to 65% by dissolving a water-insoluble chitosan having a degree of deacetylation of at least 70% in an aqueous acid solution, diluting the solution with water or a water-soluble solvent and adding an acylation agent to the diluted solution. Preferred water miscible solvents are lower monohydric alcohols such as methanol, ethanol, isopropyl alcohol, butyl alcohol, etc., polyhydric alcohols such as glycerin, propylene glycol, etc. and ketones such as acetone. Disclosed acylation agents are anhydrides of monocarbocyclic acids having from 1 to 5 carbon atoms per acyl group and benzoic acid.

U.S. Pat. No. 5,061,792 discloses the preparation of chitosan salts by suspending the chitosan in about 5 to about 50 parts by weight of a $C_1$ to $C_3$ monohydric alcohol containing an amount of water sufficient to raise the dielectric constant of the alcohol to at least about 30 and not more than about 40, adding about 0.5 to about 4 equivalents for each equivalent of amino groups in the chitosan of an acid, maintaining the mixture until reaction between the chitosan and the acid is complete, and recovering and drying the chitosan salt. The concentrations of water in the alcohol solutions ranges as follows: methanol—0%–9.7% by weight; ethanol—4.4%–13.7% by weight; 1-propanol—5.8%–13.4% by weight; 2-propanol—6.7%–14.4% by weight.

U.S. Pat. No. 4,929,722 discloses the preparation of chitosan salts in a heterogenerous reaction between dissolved organic acids and chitosan dispersed in aqueous alcohols, inter alia, containing an amount of water in an amount up to about 65 wt. % of the total medium, preferably 30 to 45 wt. %, more preferably about 40 wt. %.

The following papers disclose the reaction of chitosan with various anhydrides: (1) "Formation and Characterization of a Physical Chitin Gel," L. Vachoud et al., Carbohydrate Research 302 (1977), 169–177; (2) "Chitosan Film Acylation and Effects on Biodegradability," Jin Xu et al., Macromolecules 1996, 29, 3436–3440; (3) "N-Acetylchitosan Gel: A Polyhydrate of Chitin," Shigehero Hirans et al., Biopolymers 15 (1976), 1685–1691.

SUMMARY OF THE INVENTION

We have found that an organic diacid anhydride derivative of chitosan can be prepared under high shear conditions utilizing minor amounts of water. This process does not require non-aqueous solvents or massive steps to recover the anhydride chitosan derivative from aqueous or organic solvents. Moreover, the derivative can be neutralized in-situ with a base to provide the basic salt of the derivative which can then be dispersed in water to produce viscous, alkaline, aqueous slurries/dispersions.

It is an object of this invention to provide a method of preparing an organic diacid anhydride-modified derivative of chitosan under high shear in a solid to semi-solid state which does not require the removal of large quantities of solvents for the recovery thereof.

It is another object of this invention to provide a method of preparing a basic salt of an organic diacid anhydride-modified derivative of chitosan which will disperse in aqueous liquids to produce viscous alkaline dispersions/slurries.

Another object of the invention is to provide an anhydride-modified chitosan powder comprising an organic diacid anhydride, chitosan, and water, and optionally a basic material, wherein the weight ratio of organic diacid anhydride to chitosan is from about 0.2 to 1 to about 1 to 1, wherein the weight ratio of water to chitosan is from about 0.33 to 1 to about 1.33 to 1, and wherein the weight ratio of the basic material to chitosan is from 0 to 1 to about 1.67 to 1, preferably 0.33 to 1 to 1.33 to 1.

Still another object of this invention is to provide a method of drilling a well comprising circulating in a wellbore during drilling an aqueous alkaline liquid containing an organic diacid anhydride-modified chitosan in an amount sufficient to increase the viscosity of the liquid.

These and other objects of this invention will be apparent to one skilled in the art upon reading this specification and the appended claims.

While the invention is susceptible of various modifications and alternative forms, specific embodiments thereof will hereinafter be described in detail and shown by way of example. It should be understood, however, that it is not intended to limit the invention to the particular forms disclosed, but, on the contrary, the invention is to cover all modifications and alternatives falling within the spirit and scope of the invention as expressed in the appended claims.

The compositions can comprise, consist essentially of, or consist of the stated materials. The method can comprise, consist essentially of, or consist of the stated steps with the stated materials.

DETAILED DESCRIPTION AND PREFERRED EMBODIMENTS

It is one aspect of this invention to provide an anhydride-modified chitosan (hereinafter sometimes referred to as AMC). The AMC is prepared in a heterogeneous process by mixing together the chitosan, anhydride, and water under high shear. The relative concentrations of the chitosan, anhydride, and water in the AMC are such as to provide the desired concentrations of the chitosan and anhydride in the fluids to which the AMC is added. Generally the relative concentrations are as follows: chitosan=30% to 65% by weight; anhydride=10% to 30% by weight; and water=20% to 40% by weight. Preferably the relative concentrations are: chitosan=35% to 55%, anhydride=18% to 25%, and water= 25% to 45%; most preferably, chitosan=40% to 50%, anhydride=20% to 25%, and water=27.5% to 35%.

Exemplary mixers include the Littleford Day Double Arm Mixers, Littleford FKM and KM Mixers, with or without choppers, Littleford POLYPHASE® Mixers, Ross Double Planetary Mixer, Baker Perkins Twin-Screw Continuous Mixers, Processall Mixmill, mixer-extruders, V-blenders with intensifier bar and the like.

The addition of the chitosan, anhydride, and water can be added to the mixer in any order. Preferably the water can be added to the chitosan to hydrate it, followed by addition of the anhydride.

The AMC is generally a powder which is preferably ground before use. Preferably the particle size of the AMC is less than 60 mesh, U.S. Standard Sieve Series.

The AMC can be suspended in a liquid other than water to produce an AMC suspension suitable for addition to an alkaline aqueous liquid to increase the viscosity thereof.

The chitosan useful in the AMC will have a degree of acetylation from about 0% to about 60%, preferably from about 25% to about 55%, and most preferably from about 40% to about 50%. Thus the degree of deacetylation of the chitosan's precursor chitin is from 40% to about 100%, preferably from about 45% to about 75%, and most preferably from about 50% to about 60%.

The anhydride modifiers suitable for use in the present invention are saturated or unsaturated organic diacid anhydrides, substituted products of such anhydrides, and mixtures thereof, wherein the substituted products contain one or more functional groups selected from the group consisting of hydroxyl, carboxyl, alkenyl, amino, and mixtures thereof. Exemplary saturated anhydrides are succinic anhydride (preferred), acetoxysuccinic anhydride, methylsuccinic anhydride, diacetyl tartaric anhydride, tartaric anhydride, glutaric anhydride, glutamic anhydride, and the like. Exemplary unsaturated anhydrides used can be maleic anhydride (preferred), itaconic anhydride, citraconic anhydride, dodecenylsuccinic anhydrides, octadecenylsuccinic anhydride, other alkenyl succinic anhydrides, and the like wherein the alkenyl group contains from about 2 to about 20 carbon atoms, and mixtures thereof.

The concentration of the organic diacid anhydride in the AMC is from about 20% to about 100% of the weight of chitosan in the AMC, i.e., the weight ratio of anhydride to chitosan is from about 0.2 to 1 to about 1 to 1. It is preferred that the weight ratio of the succinic anhydride to chitosan is from about 0.33 to 1 to about 0.6 to 1.

The concentration of the water in the AMC is such that the water to chitosan weight ratio is from about 0.33 to 1 to about 1.33 to 1, preferably from about 0.5 to 1 to about 1 to 1, and most preferably from about 0.5 to 1 to about 0.8 to 1. The water can be removed, or partially removed, from the AMC, as by drying, after the AMC has been prepared by the high shear process disclosed herein.

Alkanoic acid anhydrides (alkanoic anhydrides) such as acetic anhydride, propionic anhydride, butyric anhydride, dodecanoic anhydride, and the like can be used together with the organic diacid anhydrides, if desired.

As indicated hereinbefore, the AMC set forth herein are useful in drilling a well in a rotary drilling process wherein there is circulated in a wellbore (borehole) a drilling fluid during the drilling thereof. Such processes are well known in the art. Generally, the method of drilling a well penetrating a subterranean formation comprises circulating an aqueous alkaline AMC-containing fluid as set forth herein through the well by introducing the drilling fluid into the well and into contact with the formation and withdrawing the drilling fluid from the well to remove cuttings therefrom. The fluids can be formulated for use as spotting fluids for use in releasing stuck pipe or tools within a borehole wherein the fluid is circulated to the depth in the borehole of the stuck pipe or tool and in a volume sufficient to displace the fluid in the borehole over the entire stuck area, and allowing the spotting fluid to soak for a period of time sufficient to release the stuck pipe or tool. The fluids can be formulated to provide viscous gels to overcome lost circulation problems in a wellbore as is known in the art.

The invention provides oil and gas well drilling and servicing fluids containing chitosan which is modified with one or more organic diacid anhydrides and water as hereinbefore disclosed. The fluids are useful in various operations such as drilling, fracturing, sand control, lost circulation control, completion, workover, and the like. The preferred fluids are alkaline aqueous pseudoplastic fluids having a Brookfield 0.3 rpm viscosity (hereinafter sometimes referred to as "low shear rate viscosity" or "LSRV") of at least 10,000 centipoise and a shear thinning index (hereinafter sometimes referred to as "STI") greater than about 25. The STI is the ratio of the Brookfield viscosity at 0.3 rpm to the Brookfield viscosity at 100 rpm and is an indication of the shear thinning, pseudoplastic characteristic of the fluids. Preferably the LSRV is at least about 20,000 centipoise, most preferably at least about 30,000 centipoise.

The concentration of AMC in the fluids will be sufficient to impart to the fluids the rheological characteristics desired. Generally the concentration of AMC will be from about 2 lb/bbl (0.57% w/v) to about 10 lb/bbl (2.865% w/v), preferably from about 3 lb/bbl (0.857% w/v) to about 8 lb/bbl (2.3% w/v).

The fluids are initially prepared by forming an aqueous AMC solution/dispersion and thereafter raising the pH to basic, i.e., to a pH of about 7.0 or above, preferably from about 8 to about 11.

The basic compound used to raise the pH to the alkaline range can be any compatible base which can be determined by routine testing. Preferred basic compounds are the alkali metal and ammonium hydroxides, carbonates and bisulfites, and mixtures thereof. Organic bases such as low molecular weight amines and hydroxyamines, such as ethanolamine and the like, can be used to raise the pH, also in combination with an inorganic basic compound. Preferred bases are the alkali metal carbonates.

In accordance with another embodiment of this invention, a basic material can be added to the AMC such that when the AMC is added to an aqueous solution, an alkaline aqueous solution will result into which the AMC disperses or solublizes to provide a viscous alkaline aqueous liquid.

Preferred basic materials are water soluble carbonates, acetates, phosphates and the like. Preferably the basic material is an alkali metal water soluble basic salt. Most preferably the basic material is an alkali metal carbonate, such as sodium carbonate, potassium carbonate, lithium carbonate, and mixtures thereof. Still most preferably sodium carbonate.

We have now found that incorporation of the basic material into the AMC powder enhances the aging stability of the AMC powder. This is indicated by the enhanced viscosity of the AMC solutions/dispersions obtained after aging the AMC powders and then dispersing them in aqueous liquids (alkaline aqueous liquids when the AMC does not contain the basic material). Furthermore, the basic material enhances the thermal stability of the alkaline aqueous dispersions/solutions containing the AMC.

The concentration of the basic material in the AMC is such as to provide a weight ratio of basic material to chitosan from about 0 to 1 to about 1.67 to 1, preferably from about 0.33 to 1 to about 1.33 to 1, and most preferably from about 0.5 to 1 to about 1 to 1. The preferred basic material is sodium carbonate.

The water base borehole fluids and well servicing fluids of this invention generally will contain materials well known in the art to provide various characteristics of properties to the fluid. Thus the fluids may contain one or more viscosifiers or suspending agents in addition to the chitosan, weighting agents, corrosion inhibitors, soluble salts, biocides, fungicides, seepage loss control additives, bridging agents, deflocculants, lubricity additives, shale control additives, pH control additives, and other additives as desired.

The borehole fluids may contain one or more materials which function as encapsulating or fluid loss control additives to restrict the entry of liquid from the fluid to the contacted shale. Representative materials known in the art include partially solublized starch, gelatinized starch, starch derivatives, cellulose derivatives, humic acid salts (lignite salts), lignosulfonates, gums, biopolymers, synthetic water soluble polymers, and mixtures thereof.

The oil and gas well drilling and servicing fluids of this invention preferably have a pH in the range from about 7.5 to about 11.5, most preferably from 8 to about 11.

If desired, water soluble potassium compounds can be incorporated into the fluids of this invention to increase the potassium ion content thereof. Thus it is known to add potassium chloride, potassium formate, potassium acetate, and the like to fluids to enhance the shale stabilizing characteristics of the fluids.

The well drilling and servicing fluids of this invention contains an aqueous phase which may be fresh water, a natural brine, sea water or a formulated brine. The formulated brine is manufactured by dissolving one or more soluble salts in water, a natural brine, or sea water. Representative soluble salts are the chloride, bromide, acetate and formate salts of potassium, sodium, calcium, magnesium and zinc. The preferred salts contain a monovalent cation.

The borehole fluid of this invention is circulated or spotted within a borehole during well drilling or servicing operations as is well known in the art. Fracturing fluids are used to hydraulically fracture subterranean formations as is well known in the art.

The fluids of the invention can also optionally contain one or more aldehydes to react with the AMC present in the fluids. Generally the concentration of the aldehyde will be from about 0.7 kg/m$^3$ (0.25 ppb) to about 57 kg/M$^3$ (20 ppb), preferably from about 0.7 kg/m$^3$ (0.25 ppb) to about 43 kg/m$^3$ (15 ppb).

In order to more completely describe the invention, the following non-limiting examples are given. In these examples and in this specification, the following abbreviations may be used: ml=milliliter; cp=centipoise; ppb= pounds per 42 gallon barrel; PV=API plastic viscosity in centipoise; YP=API yield point in pounds per 100 square feet; rpm=revolutions per minute; API=American Petroleum Institute; LSRV=low shear rate viscosity in centipoise as determined with a Brookfield Viscometer at 0.3 rpm; lb/100 sq.ft.=pounds per 100 square feet; kg/m$^3$=kilograms per cubic meter.

EXAMPLE 1

In a blender jar on an Osterizer 12-speed high shear blender, 15 grams of chitosan (which had been ball milled and the minus 50 mesh fraction obtained) obtained from ChitinWorks America, Inc., was moistened with the amount of water set forth in Table 1. 7.5 grams of succinic anhydride were added and the mixture was mixed on the high/grate setting for 15 minutes, stopping the blender every 3 minutes to know or scrape the powder off the side of the jar.

The anhydride-modified chitosan samples were thereafter mixed with a solution of 5 grams of sodium carbonate in 350 ml of water and sheared for 5 minutes. The amount of each AMC sample was sufficient to provide each fluid with a concentration of 4 ppb of chitosan. The viscosity of the resulting dispersions/slurries were obtained. The data obtained are set forth in Table 1.

EXAMPLE 2

In a blender jar on the Osterizer blender, 15 grams of chitosan (which had been micropulverized and the minus 50 mesh fraction obtained) obtained from ChitinWorks America, Inc., was moistened with 9 ml of water. Thereafter, the amount of succinic anhydride set forth in Table 2 was added and the mixture was mixed on the high setting for 15 minutes, stopping the blender every three minutes to knock or scrape the powder off the side of the jar.

The AMC samples were evaluated as in Example 1. The data obtained are set forth in Table 2.

EXAMPLE 3

AMC samples were prepared as in Example 1 containing the amounts of water set forth in Table 3. The chitosan used, obtained from ChitinWorks America, Inc., had been micropulverized. Additionally, each sample contained 9 ml (8.76 g) of tetraethylene-pentamine (TEPA) which was added after the succinic anhydride and mixed ten minutes while scraping the powder off the sides of the jar as before.

These AMC samples were evaluated as in Example 2 initially and after hot rolling the fluids 16 hours at 82.2° C. (180° F.). The data obtained are set forth in Table 3.

EXAMPLE 4

AMC samples were prepared as in Example 3 containing 15.0 grams chitosan, 7.5 grams of succinic anhydride, 9 ml of water, 9 ml (7.1 g) of methanol in place of the TEPA, and the amounts of soda ash set forth in Table 4. The soda ash was added after the methanol and mixed on low for 15 minutes.

The AMC samples were evaluated as in Example 2 initially and after the samples had aged at ambient temperature in sealed containers for eight weeks. The data obtained are set forth in Table 4.

TABLE 1

The Effect of the Water Content in the AMC

|  | 1-1 | 1-2 | 1-3 | 1-4 | 1-5 |
|---|---|---|---|---|---|
| Fluid Composition |  |  |  |  |  |
| Water, ml | 350 | 350 | 350 | 350 | 350 |
| Soda Ash, g | 5 | 5 | 5 | 5 | 5 |
| AMC-7 ml Water, g | 7.49 |  |  |  |  |
| AMC-8 ml Water, g |  | 7.79 |  |  |  |
| AMC-9 ml Water, g |  |  | 8.45 |  |  |
| AMC-10 ml Water, g |  |  |  | 8.61 |  |
| AMC-11 ml |  |  |  |  | 8.96 |
| Brookfield Rheology |  |  |  |  |  |
| 0.3 rpm, cp | 800 | 13697 | 35592 | 69585 | 76784 |
| 0.5 rpm, cp | 708 | 10858 | 25615 | 48470 | 53269 |
| 100 rpm, cp | 550 | 1476 | 2124 | 2405 | 2298 |

TABLE 2

The Effect of Succinic Anhydride Concentration

|  | 2-1 | 2-2 | 2-3 | 2-4 |
|---|---|---|---|---|
| Field Composition |  |  |  |  |
| Water, ml | 350 | 350 | 350 | 350 |
| Soda Ash, g | 5 | 5 | 5 | 5 |
| AMC-5.5 g Succinic Anhydride, g | 7.63 |  |  |  |
| AMC-6.5 g Succinic Anhydride, g |  | 8.11 |  |  |
| AMC-7.5 g Succinic Anhydride, g |  |  | 8.16 |  |
| AMD-9.0 g Succinic Anhydride, g |  |  |  | 8.45 |
| Fluid Evaluation |  |  |  |  |
| pH | 10.16 | 10.01 | 9.82 | 9.62 |
| Brookfield Rheology |  |  |  |  |
| 0.3 rpm, cp | 49589 | 134000 | 42691 | 44790 |
| 0.5 rpm, cp | 36472 | 81343 | 24775 | 27594 |
| 100 rpm, cp | 1752 | 2807 | 1956 | 2459 |
| Fann Rheology |  |  |  |  |
| 600 rpm reading | 149 | 190 | 171 | 201 |
| 300 rpm reading | 109 | 142 | 129 | 152 |
| Plastic Viscosity, cp | 40 | 48 | 42 | 49 |
| Yield Point, lb/100 sq.ft. | 69 | 94 | 87 | 103 |

TABLE 3

The Effect of the Water Content in AMC Containing TEPA

|  | 3-1 | 3-2 | 3-3 |
|---|---|---|---|
| Fluid Composition |  |  |  |
| Water, ml | 350 | 350 | 350 |
| Soda Ash, g | 5 | 5 | 5 |
| AMC-9 ml Water, g | 10.40 |  |  |
| AMC-12 ml Water, g |  | 11.15 |  |
| AMC-15 ml Water, g |  |  | 11.41 |
| Fluid Evaluation, Initial |  |  |  |
| pH | 10.42 | 10.33 | 10.32 |
| Brookfield Rheology |  |  |  |
| 0.3 rpm, cp | 71985 | 86382 | 96779 |
| 0.5 rpm, cp | 47750 | 55428 | 62627 |
| 100 rpm, cp | 1560 | 1488 | 1428 |
| Fann Rheology |  |  |  |
| 600 rpm reading | 160 | 143 | 144 |
| 300 rpm reading | 117 | 104 | 103 |
| Plastic Viscosity, cp | 43 | 39 | 41 |
| Yield Point, lb/100 sq.ft. | 74 | 65 | 62 |

TABLE 3-continued

The Effect of the Water Content in AMC Containing TEPA

| | 3-1 | 3-2 | 3-3 |
|---|---|---|---|
| Field Evaluation After 16 Hours Hot Rolling at 82.2° C. | | | |
| pH | 10.44 | 10.35 | 10.32 |
| Brookfield Rheology | | | |
| 0.3 rpm, cp | 168000 | 137000 | 108000 |
| 0.5 rpm, cp | 113000 | 90941 | 68145 |
| 100 rpm, cp | 1878 | 1692 | 1266 |
| Fann Rheology | | | |
| 600 rpm reading | 152 | 141 | 137 |
| 300 rpm reading | 119 | 104 | 100 |
| Plastic Viscosity, cp | 33 | 37 | 37 |
| Yield Point, lb/100 sq.ft. | 86 | 67 | 63 |

TABLE 4

The Effect of Sodium Carbonate on the Aging Stability of Chitosan Succinate

| Field Composition | 4-1 | 4-2 | 4-3 | 4-4 | 4-5 | 4-6 |
|---|---|---|---|---|---|---|
| Water, ml | 350 | 350 | 350 | 350 | 350 | 350 |
| Soda Ash, g | 5 | 3.67 | 0 | 5 | 3.67 | 0 |
| AMC-NO Soda Ash, g | 10.06 | | | 10.06 | | |
| AMC-5.0 g Soda Ash, g | | 11.38 | | | 11.38 | |
| AMC-20.0 g Soda Ash, g | | | 15.39 | | | 15.39 |
| Fluid Evaluation | Initial | | | 8 Weeks Aging | | |
| pH | 9.78 | 9.95 | 10.05 | 9.81 | 9.88 | 10.0 |
| Brookfield Rheology | | | | | | |
| 0.3 rpm, cp | 63187 | 77184 | 85982 | 4479 | 99179 | 119000 |
| 0.5 rpm, cp | 42951 | 50629 | 59747 | 3839 | 65026 | 85662 |
| 100 rpm, cp | 1710 | 1722 | 1722 | 263 | 1620 | 2573 |
| Fann Rheology | | | | | | |
| 600 rpm reading | 178 | 171 | 163 | 151 | 172 | 181 |
| 300 rpm reading | 134 | 128 | 119 | 108 | 127 | 139 |
| Plastic Viscosity, cp | 44 | 43 | 44 | 43 | 45 | 42 |
| Yield Point, lb/100 sq.ft. | 90 | 85 | 75 | 65 | 82 | 97 |
| Field Evaluation After 16 Hours Hot Rolling at 82.2° C. | | | | | | |
| pH | 9.77 | 9.89 | 10.10 | 9.81 | 10.05 | 10.09 |
| Brookfield Rheology | | | | | | |
| 0.3 rpm, cp | 87581 | 133000 | 199000 | 31593 | 121000 | 157000 |
| 0.5 rpm, cp | 60227 | 88301 | 123000 | 21595 | 76784 | 107000 |
| 100 rpm, cp | 1146 | 1494 | 2184 | 696 | 1326 | 1626 |
| Fann Rheology | | | | | | |
| 600 rpm reading | 144 | 152 | 151 | 117 | 144 | 142 |
| 300 rpm reading | 112 | 111 | 110 | 78 | 104 | 102 |
| Plastic Viscosity, cp | 32 | 41 | 41 | 39 | 40 | 40 |
| Yield Point, lb/100 sq.ft. | 80 | 70 | 69 | 39 | 64 | 62 |

What is claimed is:

1. The method of preparing an anhydride-modified chitosan comprising mixing under high shear conditions chitosan, an organic diacid anhydride, and water, wherein the concentration of the chitosan is from about 30% to about 65% by weight, the concentration of the anhydride is from about 10% to about 30% by weight and the concentration of water is from about 20% to about 40% by weight.

2. The method of claim 1 wherein the anhydride is selected from the group consisting of alkanedioic acid anhydrides, alkanedioic acid anhydrides, substituted products of such anhydrides, and mixtures thereof, wherein the substituted products contain one or more functional groups selected from the group consisting of hydroxyl, carboxyl, alkenyl, amino, and mixtures thereof.

3. The method of claim 1 wherein the anhydride is selected from the group consisting of succinic anhydride, maleic anhydride, alkenylsuccinnic anhydrides wherein the alkenyl group contains from about 2 to about 20 carbon atoms, and mixtures thereof.

4. The method of claim 1 wherein the anhydride is succinic anhydride.

5. The method of claim 1, 2, 3, or 4 wherein the weight ratio of anhydride to chitosan is from about 0.2 to 1 to about 1 to 1.

6. The method of claim 5 wherein there is additionally mixed under high shear conditions with the chitosan, organic diacid anhydride, and water, an inorganic basic material wherein the weight ratio of the inorganic basic material to chitosan is from about 0 to 1 to about 1.67 to 1.

7. The method of claim 5 wherein there is additionally mixed under high shear conditions with the chitosan, organic diacid anhydride, and water, a water soluble carbonate selected from the group consisting of sodium carbonate, potassium carbonate, lithium carbonate, and mixtures thereof, wherein the weight ratio of the carbonate to chitosan is from about 0.33 to 1 to about 1.33 to 1.

8. The method of claim 7 wherein the carbonate is sodium carbonate.

9. An anhydride-modified chitosan-containing composition comprising chitosan, an organic diacid anhydride, water, and optionally a basic material, wherein the weight ratio of anhydride to chitosan is from about 0.2 to 1 to about 1 to 1, wherein the weight ratio of water to chitosan is from about 0.33 to 1 to about 1.33 to 1, and wherein the weight ratio of the basic material to chitosan is from about 0 to 1 to about 1.67 to 1.

10. The anhydride-modified chitosan-containing composition of claim 9 wherein the anhydride is selected from the group consisting of alkenedioic acid anhydrides, alkanedioic acid anhydrides, substituted products of such anhydrides, and mixtures thereof, wherein the substituted products contain one or more functional groups selected from the group consisting of hydroxyl, carboxyl, alkenyl, amino, and mixtures thereof.

11. The anhydride-modified chitosan-containing composition of claim 9 wherein the anhydride is selected from the group consisting of succinic anhydride, maleic anhydride, alkenyl succinic anhydrides wherein the alkenyl group contains from about 2 to about 20 carbon atoms, and mixtures thereof.

12. The anhydride-modified chitosan-containing composition of claim 9 wherein the anhydride is succinic anhydride and wherein the basic material is an alkali metal carbonate.

13. The anhydride-modified chitosan-containing composition of claim 12 wherein the carbonate is sodium carbonate.

14. The anhydride-modified chitosan-containing composition of claim 13 wherein the weight ratio of sodium carbonate to chitosan is from about 0.33 to 1 to about 1.33 to 1.

15. A method of drilling a well wherein a drilling fluid is circulated in the wellbore during drilling comprising circulating as the drilling fluid an aqueous alkaline fluid having dispersed or solublized therein the anhydride-modified chitosan-containing composition of claim 9, 10, 11, 12, 13, or 14.

* * * * *